United States Patent [19]

Knifton et al.

[11] 4,332,915

[45] Jun. 1, 1982

[54] PRODUCTION OF ALKANOLS FROM SYNTHESIS GAS

[75] Inventors: John F. Knifton; Jiang-Jen Lin, both of Austin, Tex.

[73] Assignee: Texaco Inc., White Plains, N.Y.

[21] Appl. No.: 279,885

[22] Filed: Jul. 2, 1981

[51] Int. Cl.$^3$ .............................................. C07C 27/06
[52] U.S. Cl. .................................... 518/700; 252/428; 252/430; 252/472
[58] Field of Search ................................ 518/700, 715

[56] References Cited

U.S. PATENT DOCUMENTS 4,088,671 5/1978 Kobylinski .......................... 518/715
4,265,828 5/1981 Knifton .............................. 518/700

Primary Examiner—Howard T. Mars
Attorney, Agent, or Firm—Carl G. Ries; Jack H. Park; Walter D. Hunter

[57] ABSTRACT

This invention concerns a process of making alkanols and particularly ethanol which comprises contacting a mixture of CO and $H_2$ at a pressure of 500 psig or greater and at a temperature of at least 150° C. with a catalyst system comprising a ruthenium-containing compound and a cobalt-containing compound dispersed in a low melting quaternary phosphonium or ammonium base or salt.

17 Claims, No Drawings

PRODUCTION OF ALKANOLS FROM SYNTHESIS GAS

BACKGROUND OF THE INVENTION

1. Field of the Invention

This invention concerns an improved process for preparing alkanols by reaction of oxides of carbon with hydrogen in presence of a catalyst system.

2. Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C. or more using as a catalyst a mixture of copper, chromium and zinc oxides. A wide variety of other catalysts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed.

One serious problem associated with synthesis gas operations in the part has been the non-selectivity of the product distribution since high activity catalysts generally yield a liquid product containing numerous hydrocarbon materials. Thus, complicated recovery schemes are necessary to separate the desired products and the overall yield of the valuable organic products is low. This is a definite need in the art for a process which will produce alkanols and especially ethanol-rich alkanols with a high degree of selectivity from synthesis gas.

This invention therefore is to provide a process of making alkanols by resort to a unique catalyst system which produces said alkanols in good yields and with excellent selectivity especially with regard to ethanol formation.

SUMMARY OF THE INVENTION

This invention concerns a method for making alkanols which comprises contacting a mixture of CO and $H_2$ at a pressure of 500 psig or greater and at a temperature of at least 150° C. with a catalyst system comprising a ruthenium-containing compound and a halogen-free cobalt-containing compound dispersed in a low melting quaternary phosphonium or ammonium base or salt.

DETAILED DESCRIPTION OF THE INVENTION

In the narrower and more preferred practice of this invention, alkanols and especially ethanol, are prepared by contacting a mixture of CO and $H_2$ at a temperature of about 180° to about 250° C. and at a pressure of 2000 psig or greater with a catalyst system comprising one or more ruthenium-containing compounds and one or more halogen-free cobalt-containing compounds dispersed in a low melting quaternary phosphonium base or salt of an organic or mineral acid.

As previously pointed out the catalyst system employed in the practice of this invention contains one or more ruthenium-containing compounds and one or more halide-free cobalt-containing compounds. The ruthenium-containing catalyst as well as the halogen-free cobalt-containing catalyst may be chosen from a wide variety of organic or inorganic compounds, complexes, etc., as will be shown and illustrated below. It is only necessary that the catalyst precursor actually employed contain the said metals in any of their ionic states. The actual catalytically active species is then believed to comprise ruthenium and cobalt in complex combination with carbon monoxide and hydrogen. The most effective catalysis is believed to be achieved where ruthenium and cobalt hydrocarbonyl species are solubilized in a quaternary salt under reaction conditions.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II) iodide, anhydrous ruthenium(III) chloride and ruthenium nitrate, or as the salt of a suitable organic carboxylic acid, for example, ruthenium(III) acetate, ruthenium napthhenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The cobalt-containing catalyst precursors may take many different forms. For instance, the cobalt may be added to the reaction mixture in an oxide form, as in the case of, for example, cobalt(II) oxide (CoO) or cobalt-(II, III) oxide ($Co_3O_4$). Alternatively, it may be added as the halogen-free salt of a mineral acid, as in the case of cobalt(II) nitrate, hydrate ($Co(NO_3)_2.6H_2O$), cobalt-(II) sulphate, etc., or as the salt of a suitable organic carboxylic acid, for example, cobalt(II) formate, cobalt-(II) acetate, cobalt(II) propionate, cobalt(II) oxalate, cobalt naphthenate, as well as cobalt complexes with carbonyl-containing ligands as in the case of cobalt(II) acetylacetonate and cobalt(III) acetylacetonates, etc. The cobalt may also be added to the reaction zone as cobalt carbide, cobalt(II) carbonate and a carbonyl or hydrocarbonyl derivative. Here, suitable examples include dicobalt octacarbonyl ($Co_2(CO)_8$), cobalt hydrocarbonyl (HCo(CO)$_4$) and substituted carbonyl species such as the triphenyl phosphine cobalt tricarbonyl dimer, etc.

Preferred cobalt-containing compounds include oxides of cobalt, cobalt salts of organic carboxylic acids and cobalt carbonyl or hydrocarbonyl derivatives. Among these, particularly preferred are cobalt(II) acetylacetonate, cobalt(III) acetylacetonate, cobalt(II) acetate, cobalt(II) propionate, and dicobalt octacarbonyl.

The ruthenium-containing compound are, prior to their catalytic use in making alkanols, first dispersed in a low melting quaternary phosphonium or ammonium base or salt. It is interesting to note that the ruthenium-containing compound alone, without being dispersed in said salt or base, has little, if any activity in promoting the manufacture of alkanols from synthesis gas.

The quaternary phosphonium or ammonium base or salt must be relatively low melting, that is, melt at a temperature less than about the temperature of reaction of making alkanols. Usually the quaternary compound has a melting point less than about 180° C., and most often has a melting point less than 150° C.

Suitable quaternary phosphonium salts have the formula:

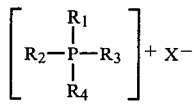

where R$_1$, R$_2$, R$_3$ and R$_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance. Also useful are the corresponding quaternary ammonium bases and salts in the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more C$_1$-C$_{10}$ alkyl substituents, bonded to the phosphorus or nitrogen atom through the aryl function.

Illustrative examples of suitable quaternary phosphonium and ammonium bases and salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetraethylammonium bromide, and trimethyldodecylammonium bromide. Table I and provides evidence of the effectiveness of the quaternary ammonium and phosphonium salts when in combination with ruthenium(IV) oxide and ruthenium(III) acetylacetonate.

The preferred quaternary salts are generally the tetralkylphosphonium salts containing alkyl groups having 1-6 carbon atoms, such as methyl, ethyl, and butyl. Tetrabutylphosphonium salts, such as tetrabutylphosphonium bromide, are most preferred for the practice of this invention.

Preferred tetrabutylphosphonium salts or bases include the bromide, chloride, iodide, acetate and chromate salts and hydroxide base.

Generally, in the catalyst system the molar ratio of the ruthenium compound to the quaternary phosphonium or ammonium salt or base will range from about 1:0.01 to about 1:100 or more and, preferably, will be from about 1:0.5 to about 1:20.

The quantity of ruthenium compound and the cobalt compound employed in the instant invention is not critical and may vary over a wide range. In general, the novel process is desirably conducted in the presence of a catalytically effective quantity of the active ruthenium species and of the cobalt species which gives the desired product in reasonable yield. The reaction proceeds when employing as little as about $1 \times 10^{-6}$ weight percent, and even lesser amounts, or ruthenium together with about $1 \times 10^{-6}$ weight percent or less of cobalt, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 weight percent in conjunction with a cobalt concentration of from about $1 \times 10^{-5}$ to about 5 weight percent, based on the total weight of reaction mixture is generally desirable in the practice of this invention. The preferred ruthenium-to-cobalt atomic ratio is from 10:1 to 1:10.

The temperature range which can usefully be employed in these syntheses is a variable dependent upon other experimental factors, including the pressure, and the concentration and choice of the particular species of ruthenium catalyst among other things. The range of operability is from about 150° C. to 350° C. when superatmospheric pressure of syngas are employed. A narrow range of 180° to 250° C. represents the preferred temperature range.

Superatmospheric pressures of 500 psi or greater lead to substantial yields of alkanols by the process of this invention. A preferred operating range is from 2000 psi to 9000 psi, although pressures above 9000 psi also provide useful yields of the desired alkanols.

The relative amounts of carbon monoxide and hydrogen which may be initially present in the syngas, i.e., synthesis gas, mixture are variable, and these amounts may be varied over a wide range. In general, the mole ration of CO:H$_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of monocarboxyl acids may also be formed during the course of this desired alkanol synthesis. Most often these are ester derivatives of acetic acid such as methyl acetate, ethyl acetate, propyl acetate, etc. These esters and the individual alkanols formed can be conveniently recovered from the reaction mixture by distillation, extraction, etc.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alkanol product, and said material may be recovered by methods well known in the art, such as distillation, fractionation, extraction and the like. A fraction rich in the ruthenium and cobalt catalyst components may then be recycled to the reaction zone, if desired, and additional products generated.

The products have been identified in this work by one or more of the following analytical procedures, viz., gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Various embodiments of the process of this invention are illustrated in the following examples which are to be considered not limitative.

EXAMPLE 1

This example illustrates a typical synthesis of ethanol-rich alkanols catalyzed by ruthenium-plus cobalt-containing compounds dispersed in sample of low-melting (m.p.100° C.) tetrabutylphosphonium bromide salt.

A mixture of ruthenium(IV) oxide (4 mmoles) and cobalt(III) acetylacetonate (4 mmoles) dispersed in tetrabutylphosphonium bromide (10.0 g) was transferred in a glass liner under $N_2$ purge, to an 850 ml capacity pressure reactor equipped with heating and means of agitation. The reactor was sealed, flushed with a mixture of carbon monoxide and hydrogen (1:1 molar) and pressured to 2000 psig with the same carbon monoxide-hydrogen mixture. The mixture was heated to 220° C. with rocking, the pressure raised to 4000 psig by addition of the carbon monoxide-hydrogen mixture from a large surge tank, and the reactor held at temperature for 18 hours. Pressure in the reactor is maintained at ca. 4000 psig by incremental additions of the carbon monoxide-hydrogen mixture from the surge tank.

On cooling, the reactor pressure (2100 psig) was noted, a typical gas sample taken, and the excess gas removed. The reddish-brown liquid product (38.4 g) was analyzed by glc and Karl-Fischer titration and the following results were obtained:

| 28.2 wt. % ethanol | 5.9 wt. % methyl acetate |
| 10.2 wt. % methanol | 19.9 wt. % ethyl acetate |
| 13.7 wt. % n-propanol | 9.5 wt. % propyl acetate |

-continued

| 2.0 wt. % n-butanol | 2.6 wt. % water |

The liquid yield increase was:

$$\frac{38.4 - 12.2}{12.2} \times 100 = 215 \text{ wt. \%}$$

The alkanol and acetate ester product fractions were recovered from the crude liquid product by fractional distillation in vacuo. Distillate fractions showed high alcohol content. The dark-red liquid residue (11.4 g) resolidified upon cooling.

Analyses of typical off-gas samples showed the presence of:

| 27% hydrogen | 44% carbon dioxide |
| 12% carbon monoxide | 11% methane |

The dark-red residual catalyst (supra) was then recycled to the glass-lined pressure reactor, pressured with synthesis gas and heated to 220° C. using the procedures outlined above. After reaction, 36.3 g of crude liquid product was recovered from the reactor. Analysis showed this to contain:

26.1 wt. % ethanol
11.0 wt. % methanol
11.8 wt. % propanol

The liquid yield increase was 218 wt. %.

The alkanol and acetate ester fractions were recovered from the crude liquid product by fractional distillation. Distillate fractions showed high alcohol content. The dark-red liquid residue (9.7 g) resolidified upon cooling.

This residual catalyst was returned to the pressure reactor with additional synthesis gas and conversion to liquid alkanols was conducted once more as outlined above.

An analysis of the liquid product (30.1 g) after this third catalyst cycle showed the presence of:

| 16.5 wt. % ethanol |
| 6.6 wt. % methanol |
| 5.6 wt. % n. propanol |

Complete yield data are summarized in Table I, Examples 1, 1-a, and 1-b.

EXAMPLES 2–9

Details relating to a number of additional examples (i.e., Examples 2–9) which were conducted in the same manner as Example 1 are given in Table I which follows. Here it may be noted that a number of ruthenium and cobalt carbonyl and acetylacetonate salt combinations, with different Co/Ru atomic ratios, when dispersed in tetrabutylphosphonium bromide and tetraethylammonium bromide, have been found to yield the desired ethanol rich alkanols.

A range of operating pressures and different synthesis gas ($CO/H_2$) ratios have also been found useful in the preparation of these alcohols.

TABLE I

| Example | Catalyst | Melt | Press. psi | Temp. °C | LIQUID PRODUCT COMPOSITION (WT. %) | | | | | | | | Liquid Yields % |
|---|---|---|---|---|---|---|---|---|---|---|---|---|---|
| | | | | | Alcohols | | | | Acetate Esters | | | $H_2O$ | |
| | | | | | MeOH | EtOH | PrOH | BuOH | Methyl | Ethyl | Propyl | | |
| 1 | $RuO_2$—$Co(acac)_3$ | $Bu_4PBr$ | 4000 | 220 | 10.2 | 28.2 | 13.7 | 2.0 | 5.9 | 19.9 | 9.5 | 2.6 | 215 |
| 1-a | Example 1 recycle | | 4000 | 220 | 11.0 | 26.1 | 11.8 | | 8.6 | 23.6 | 9.2 | 1.4 | 218 |
| 1-b | Example 1-a recycle | | 4000 | 220 | 6.6 | 16.5 | 5.6 | 0.8 | 10.1 | 33.6 | 14.7 | 1.1 | 210 |
| 2 | $RuO_2$—½ $Co(acac)_3$ | $Bu_4PBr$ | 4000 | 220 | 10.7 | 28.6 | 9.3 | 3.1 | 4.7 | 18.7 | 6.8 | 3.3 | 192 |
| 3 | $RuO_2$—$2Co(acac)_3$ | $Bu_4PBr$ | 4000 | 220 | 8.0 | 17.1 | 12.7 | 2.1 | 7.2 | 19.8 | 10.9 | 2.0 | 137 |
| 4 | $RuO_2$—$Co(acac)_3$ | $Bu_4PBr$ | 4000[a] | 220 | 6.8 | 7.6 | 1.6 | 1.0 | 0.8 | 0.6 | 1.9 | 76.2 | 107 |
| 5 | $Ru(acac)_3$—$Co(acac)_3$ | $Bu_4PBr$ | 4000[b] | 220 | 19.0 | 23.9 | 9.5 | 5.6 | 13.6 | 16.0 | 7.7 | 1.4 | 128 |
| 6 | $RuO_2$—$Co(acac)_3$ | $Bu_4PBr$ | 3215[c] | 220 | 7.3 | 22.2 | 9.5 | 5.6 | 1.0 | 7.3 | 11.8 | 4.4 | 37 |
| 7 | $RuO_2$—$Co(acac)_3$ | $Bu_4PBr$ | 6590[d] | 220 | 2.9 | 30.8 | 12.3 | 2.1 | 1.6 | 15.3 | 8.3 | 7.3 | 98 |
| 8 | $RuO_2$—$Co_2(CO)_8$ | $Bu_4PBr$ | 6500[d] | 220 | 3.5 | 29.6 | 15.2 | 2.4 | 2.2 | 15.7 | 7.1 | 8.6 | 110 |
| 9 | $Ru_3(Co)_{12}$—$Co_2(CO)_8$ | $Et_4NBr$ | 4000 | 220 | 2.5 | 20.3 | 11.0 | 0.2 | 7.2 | 27.1 | 19.5 | 0.6 | 66 |

[a]Run using H2/CO(2:1 molar) gas.
[b]Run for 6 hours.
[c]Initial pressure 2000 psi, variable pressure run.
[d]Initial pressure 4000 psi, variable pressure run.
acac = acetylacetonate

COMPARATIVE EXAMPLE 10

This example illustrates the inactivity of the cobalt catalyst component alone, in the absence of ruthenium, when dispersed in tetrabutylphosphonium bromide.

Following the procedures of Example I, the glass-lined reactor was charged with a mixture of cobalt octacarbonyl (3.0 mmole) dispersed in tetrabutylphosphonium bromide (10.0 g). The reactor was flushed with Co/H2, pressured to 4000 psi with carbon monoxide and hydrogen (1:1 molar) and heated to 220° C. with rocking. After 18 hours at temperature the reactor was cooled, gas sample taken, and the excess gas removed.

A green, crystalline solid product (10.9 g) was recovered from the reactor. There was no liquid product.

The liquid yield increase was <5 percent.

EXAMPLE 11

A mixture of triruthenium dodecacarbonyl (4 mmole Ru) and dicobalt octacarbonyl (4 mmole Co) dispersed in tetrabutylphosphonium bromide (10.0 g) was transferred in a glass liner under $N_2$ purge, to an 850 ml capacity pressure reactor equipped with heating and means of agitation. The reactor was sealed, flushed with a mixture of carbon monoxide and hydrogen (1:1 molar) and pressured to 2000 psig with the same carbon monoxide-hydrogen mixture. The mixture was heated to 220° C. with rocking, the pressure raised to 4000 psig by addition of the carbon monoxide-hydrogen mixture from a large surge tank, and the reactor held at temperature for 18 hours. Pressure in the reactor is maintained at ca. 4000 psig by incremental additions of the carbon monoxide-hydrogen mixture from the surge tank.

On cooling, the reactor pressure (2100 psig) was noted, a typical gas sample taken, and the excess gas removed. The reddish-brown liquid product (38.0 g) was analyzed by glc and Karl-Fischer titration and the following results were obtained:

| | |
|---|---|
| 29.1 wt. % ethanol | 7.0 wt. % methyl acetate |
| 9.3 wt. % methanol | 21.1 wt. % ethyl acetate |
| 12.6 wt. % n-propanol | 11.9 wt. % propyl acetate |
| 1.6 wt. % n-butanol | 0.4 wt. % water |

The liquid yield increase was 230 percent. The alkanol and acetate ester product fractions were recovered from the crude liquid product by fractional distillation in vacuo. Distillate fractions showed high alcohol content. The dark-red liquid residue (11.2 g) resolidified upon cooling.

It is claimed:

1. A process for making alkanols which comprises contacting a mixture of CO and H2 at a pressure of 500 psig or greater and at a temperature of at least 150° C. with a catalyst system comprising a ruthenium-containing compound and a halogen-free cobalt-containing compound dispersed in a low melting quaternary phosphonium or ammonium base or salt.

2. The process of claim 1 wherein the process is conducted at a pressure of about 2000 psi to about 9000 psi.

3. The process of claim 1 wherein the process is conducted at a temperature of about 150° C. to about 350° C.

4. The process of claim 1 wherein said quaternary salt or base has a melting point less than about 180° C.

5. The process of claim 1 wherein said quaternary salt is a tetraalkylphosphonium salt.

6. The process of claim 5 wherein said alkyl groups contain 1–6 carbon atoms.

7. The process of claim 1 wherein said quaternary is a mixed alkylaryl phosphonium quaternary.

8. The process of claim 1 wherein said quaternary salt is tetrabutylphosphonium salt.

9. The process of claim 6 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

10. The process of claim 1 wherein the ruthenium-containing compound is selected from the group consisting of one or more oxides of ruthenium, ruthenium salts of an organic carboxylic acid, ruthenium complexes with carbonyl-containing ligands and ruthenium carbonyl or hydrocarbonyl derivatives.

11. The process of claim 1 wherein the said ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecarbonyl.

12. The process of claim 1 wherein said ruthenium-containing compound is ruthenium(IV) dioxide.

13. The process of claim 1 wherein said ruthenium-containing compound is ruthenium(III) acetylacetonate.

14. The process of claim 1 wherein the said cobalt-containing compound is selected from the group consisting of one or more oxides of cobalt, cobalt salts of an organic carboxylic acid, cobalt complexes with carbonyl-containing ligands, and cobalt carbonyl and hydrocarbonyl derivatives.

15. The process of claim 1 wherein the said cobalt-containing compound is selected from the group consisting of dicobalt octacarbonyl, cobalt(III) acetylacetonate, cobalt(II) acetate, cobalt(II) propionate, and cobalt(II) acetylacetonate.

16. The process of claim 1 wherein the said cobalt-containing compound is cobalt(III) acetylacetonate.

17. The process of claim 1 wherein the said cobalt-containing compound is dicobalt octacarbonyl.

* * * * *